(12) United States Patent
Ahola et al.

(10) Patent No.: US 10,656,163 B2
(45) Date of Patent: May 19, 2020

(54) METHOD FOR DETERMINING RISK OF PRE-ECLAMPSIA

(71) Applicant: Wallac Oy, Turku (FI)

(72) Inventors: Tarja Ahola, Turku (FI); Heikki Kouru, Raisio (FI); Mikko Sairanen, Masku (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 15/508,135

(22) PCT Filed: Sep. 1, 2015

(86) PCT No.: PCT/FI2015/050566
§ 371 (c)(1),
(2) Date: Mar. 2, 2017

(87) PCT Pub. No.: WO2016/034767
PCT Pub. Date: Mar. 10, 2016

(65) Prior Publication Data
US 2017/0285041 A1    Oct. 5, 2017

(30) Foreign Application Priority Data

Sep. 2, 2014  (FI) ..................................... 20145762

(51) Int. Cl.
*G01N 33/68* (2006.01)
*G01N 33/74* (2006.01)

(52) U.S. Cl.
CPC ........... *G01N 33/689* (2013.01); *G01N 33/74* (2013.01); *G01N 2333/70564* (2013.01); *G01N 2800/368* (2013.01)

(58) Field of Classification Search
None
See application file for complete search history.

(56) References Cited

U.S. PATENT DOCUMENTS

| | | | |
|---|---|---|---|
| 6,573,103 B1 | 6/2003 | Wald | |
| 6,735,529 B1 | 5/2004 | Wald et al. | |
| 8,647,832 B2 | 2/2014 | Cuckle et al. | |
| 8,673,582 B2 | 3/2014 | Cuckle et al. | |
| 8,932,823 B2 | 1/2015 | Cuckle et al. | |
| 2004/0038305 A1 | 2/2004 | Poston et al. | |
| 2005/0255114 A1 | 11/2005 | Labat et al. | |
| 2007/0178530 A1 | 8/2007 | Poston et al. | |
| 2009/0011429 A1 | 1/2009 | Poston et al. | |
| 2012/0135427 A1* | 5/2012 | Kypros | G01N 33/74 435/7.92 |
| 2013/0344503 A1 | 12/2013 | Cuckle et al. | |
| 2014/0113319 A1 | 4/2014 | Cuckle et al. | |
| 2014/0113320 A1 | 4/2014 | Cuckle et al. | |
| 2014/0273025 A1* | 9/2014 | Hurskainen | G01N 33/689 435/7.92 |

FOREIGN PATENT DOCUMENTS

| | | |
|---|---|---|
| EP | 2368119 A1 | 9/2011 |
| WO | 02037120 | 5/2002 |
| WO | 07083099 | 7/2007 |
| WO | 2010122231 A1 | 10/2010 |
| WO | 2014078622 A1 | 5/2014 |

OTHER PUBLICATIONS

Akolekar et al., Hypertension in Pregnancy, 2011; 30: 311-321. (Year: 2011).*
Akolekar et al., Prenat Diagn 2011; 31: 66-74 (Year: 2011).*
Coomarasamy et al., Obstet Gynecol 2003; 101:1319-32 (Year: 2003).*
Finnish Patent and Registration Office, Search Report issued in FI20145762, dated Mar. 31, 2015.
Akolekar, R. et al., "Prediction of early, intermediate and late pre-eclampsia from maternal factors, biophysical and biochemical markers at 11-13 weeks". Prenatal Diagnosis, Jan. 2011, vol. 31, No. 1, pp. 66-74, DOI: 10.1002/pd.2660.
Perni, U. et al., "Angiogenic factors in superimposed preeclampsia: a longitudinal study of women with chronic hypertension during pregnancy". Hypertension, Mar. 2012, vol. 59, No. 3, pp. 740-746. DOI: 10.1161/HYPERTENSIONAHA.111.181735.
Maynard, S. E. et al., "Gestational angiogenic biomarker patterns in high risk preeclampsia groups". American Journal of Obstetrics & Gynecology. Jul. 2013, vol. 209, No. 1, ppl. 53.e1-53.e9. DOI: 10.1016/j.ajog.2013.03.017.
Sunderji, S. et al., "Automated assays for sVEGF R1 and PlGF as an aid in the diagnosis of preterm preeclampsia: a prospective clinical study". American Journal of Obstetrics & Gynecology, Jan. 2010, vol. 202, No. 1, pp. 40. e1-40.e7. DOI: 10.1016/j.ajog.2009.07.025.
Powers, R. W. et al., "Soluble fms-like tyrosine kinase 1 (sFlt1), endoglin and placental growth factor (PlGF) in preeclampsia among high risk pregnancies". PLoS One, Oct. 11, 2010, vol. 5, No. 10, e13263 [serial online], [retrieved on Mar. 17, 2015]. Retrieved from the Internet: <URL: http://dx.plos.org/10.1371/journal.pone.0013263>, <DOI: 10.1371/journal.pone.0013263>.
Sibai, B. M. et al., "Serum inhibin A and angiogenic factor levels in pregnancies with previous preeclampsia and/or chronic hypertension: are they useful markers for prediction of subsequent preeclampsia?" Amercian Journal of Obstetrics & Gynecology, Sep. 2008, vol. 199, No. 3, pp. 268.e1-268.e9. DOI: 10.1016/j.ajog.2008.06.071.
Dover, N. et al., "Placental growth factor: as an early second trimester predictive marker for preeclampsia in normal and high-risk pregnancies in a Turkish population". The Journal of Obstetrics and Gynecology of India, Jun. 2013, vol. 63, No. 3, pp. 158-163. DOI: 10.1007/s13224-012-0279-9.

(Continued)

Primary Examiner — Christina M Borgeest
(74) Attorney, Agent, or Firm — Fish & Richardson P.C.

(57) ABSTRACT

The present description relates to a method for determining the risk of a pregnant woman with chronic hypertension developing early or late onset pre-eclampsia. The present description provides methods useful for determining risk that a pregnant individual with chronic hypertension will develop an early pre-eclampsia or late pre-eclampsia. Useful combination of biochemical markers including PlGF and sP-Selectin and related clinical population studies are described herein.

1 Claim, 8 Drawing Sheets

(56) References Cited

OTHER PUBLICATIONS

Metz, T. D. et al., "Preeclampsia in high risk women is characterized by risk group-specific abnormalities in serum biomarkers". American Journal of Obstetrics & Gynecology, Nov. 2014, vol. 211, No. 5, pp. 512.e1-512.e6. Available from the Internet (ePub) Apr. 23, 2014. DOI: 10.1016/j.ajog.2014.04.027.
Poon et al., "Combined Screening for Preeclampsia and Small for Gestational Age at 11-13 Weeks", Fetal Diagnosis and Therapy, 2013, vol. 33, pp. 16-27. DOI: 10.1159/000341712.
Akolekar, R. et al., "Maternal plasma P-selectin at 11 to 13 weeks of gestation in hypertensive disorders of pregnancy". Hypertension in Pregnancy 2011; 30(3): 311-21. [Early Online: 1-13, 2010]. ISSN: 1064-1995 print / 1525-6065 online. DOI: 10.3109/10641950903242683.
Palomaki, G. E. et al., "Maternal serum α-fetoprotein, age and Down syndrome risk", American Journal of Obstetrics & Gynecolgy, 1987, vol. 156, No. 2, pp. 460-463.
Norgaard-Pedersen, B. et al., "Maternal serum markers in screening for Down syndrome", Clinical Genetics 1990; 37: 35-43.
Cuckle, H. S. et al., "Estimating a woman's risk of having a pregnancy associated with Down's syndrome using her age and serum alphafetoprotein level", British Journal of Obstetrics & Gynecology 1987, 94: 387-402.
Grudzinskas, J. G. et al. (eds.), "Screening for Down's Syndrome", Cambridge University Press, 1994.
Spencer, K. et al., "Free beta human choriogonadotropin in Down's syndrome screening: a multicentre study of its role compared with other biochemical markers", Ann Clin Biochem 1992; 29: 506-18.
Youssef, A. et al., "Uterine artery Doppler and biochemical markers (PAPP-A, PIGF, sFlt-1, P-selectin, NGAL) at 11+0 to 13+6 weeks in the prediction of late (>34 weeks) pre-eclampsia", Prenatal Diagnosis, vol. 31, Oct. 1, 2011, pp. 1141-1146, XP055223918, GB ISSN: 0197-3851, DOI: 10.1002/pd.2848.
Davey, D. A. et al., "The classification and definition of the hypertensive disorders of pregnancy", American Journal of Obstetrics & Gynecology, 1988, vol. 158, No. 1, pp. 892-898.
Akolekar et al., "Maternal serum placental growth factor at 11+0 to 13+6 weeks of gestation in the prediction of pre-eclampsia," Ultrasound Obstet. Gynecol., 2008, 32:732-739.
AU Office Action, in Australian Application No. 2009206243, dated Aug. 21, 2013, 5 pages.
AU Office Action, in Australian Application No. 2009206243; dated Jun. 6, 2014, 4 pages.
AU Office Action, in Australian Application No. 2014259509, dated Jun. 30, 2016, 3 pages.
Barnes et al., "Setting truncation limits for marker values in medical screening," J. Med. Screen, 2005, 14:103-106.
Bersinger et al., "Pre-eclampsia: increased, unchanged, and decreased serum markers in comparison to healthy third trimester pregnancy, A synopsis," Immuno-analyse et biologie spécialisée, 2005, 20:353-359.
Bersinger et al., "Pregnancy-associated and placental proteins in the placental tissue of normal pregnant women and patients with pre-eclampsia at term," Eur. J. Endocrinol., 2002, 147:785-793.
Bersinger et al., "Second- and third-trimester serum levels of placental proteins in preeclampsia and small-for-gestational age pregnancies," Acta Obstet. Gynecol. Scand., 2004, 83:37-45.
Bersinger et al., "Second-trimester serum levels of placenta growth factor (PLGF) an inhibin A are increased in smokers. Implications for pre-eclampsia risk assessment," Immuno-analyse et biologie spécialisée, 2007, 22:19-23.
Canadian Office Action in Canadian Application No. 2,713,229, dated Nov. 6, 2015, 5 pages.
Caritis et al., "Predictors of pre-eclampsia in women at high risk," Am J Obstet Gynecol, 1998, 179:946-951.
Chinese Office Action in Chinese Application No. 201410206612.6, dated Dec. 22, 2015, 2 pages, (English Translation).
Chinese Office Action in Chinese Application No. 201410206612.6, dated Jun. 3, 2015, 3 pages, (English Translation).
Chinese Office Action, in Chinese Application No. 200980110513.5; dated Aug. 16, 2013, 5 pages, (English Translation).
Chinese Office Action; in Chinese Application No. 200980110513.5; dated Jan. 14, 2013, 2 pages, (English Translation).
Cnossen, "Accuracy of mean arterial pressure and blood pressure measurements in predicting pre-eclampsia: systematic review and meta-analysis," BMJ, 2008, 1-7.
De Vivo et al., "Endoglin, PIGF and sFlt-1 as markers for predicting pre-eclampsia," Acta Obstetricia et Gynecologica, 2008, 87:837-842.
European Examination Report; in Application No. 09704269.1-1223; dated Feb. 8, 2012, 5 pages.
European Examination Report; in Application No. 09704269.1-1223; dated May 9, 2011, 15 pages.
European Office Action in European Application No. 13177423.4, dated Mar. 19, 2015, 5 pages.
European Office Action, in European Application No. 09704269.1-1405; dated Apr. 8, 2013; 5 pages.
European Patent Office, Communication of a Notice of Opposition Issued in EP Application No. 09704269.1 dated Apr. 7, 2015, 75 pages.
European Patent Office, Communication of a Notice of Opposition Issued in EP Application No. 09704269.1 dated Mar. 25, 2015, 2 pages.
European Search Report in European Application No. 13177423.4, dated Jan. 17, 2014, 7 pages.
European Search Report in European Application No. 13177423.4, dated Sep. 12, 2013, 6 pages.
India Office Action in India Application No. 6032/DELNP/2010, dated Mar. 22, 2016, 2 pages, (English Translation).
International Preliminary Report on Patentability for PCT/US2009/032062, dated Apr. 10, 2009, 7 pages.
International Search Report for International Application No. PCT/US 09/32062, dated Apr. 10, 2009, 2 pages.
Irion et al., "Prediction of pre-eclampsia, low birthweight for gestation and prematurity by uterine artery blood flow velocity waveforms analysis in low risk nulliparous women," British Journal of Obstetrics and Gynecology, 1998, 105:422-429.
Isenbruck Bosl Horschler LLP, Notice of Opposition by Roche Diagnostics GmbH received in EP Application No. 09704269.1 on Mar. 17, 2015, including annexes 1-5, 46 pages.
Khaw et al., "Maternal cardiac function and uterine artery Doppler at 11-14 weeks in the prediction of pre-eclampsia in nulliparous women," BJOG, 2008, 115:369-376.
Konijnenberg et al., "Can flow cytometric detection of platelet activation early in pregnancy predict the occurrence of preeclampsia? A prospective study." American Journal of Obstetrics & Gynecology, 1997, 177(2):434-442.
Lambert-Messerlian et al., "Placenta growth factor levels in second-trimester maternal serum in Down syndrome pregnancy and in the prediction of preeclampsia," Prenat. Diagn., 2004, 24:876-880.
Nikolaides et al., "A novel approach to first-trimester screening for early pre-eclampsia combining serum PP-13 and Doppler ultrasound", Ultrasound Obstet Gynecol, 2006, 27:13-17.
Odegard et al., "Risk factors and clinical manifestations of pre-eclampsia," BJOG, 2000, 107:1410-1416.
Papageorghiou et al., "Assessment of risk for the development of pre-eclampsia by maternal characteristics and uterine artery Doppler", BJOG: an International Journal of Obstetrics and Gynaecology, 2005, 112:703-709.
Pilalís et al., "Screening for pre-eclampsia and fetal growth restriction by uterine artery Doppler and PAPP-A at 11-14 weeks' gestation," Ultrasound Obstet. Gynecol., 2007, 29:135-140.
Plasencia et al., "Uterine artery Doppler at 11+0 to 13+6 weeks in the prediction of pre-eclampsia," Ultrasound Obstet. Gynecol., 2007, 30:742-749.
Poon et al., "First-trimester maternal serum pregnancy-associated plasma protein-A and pre-eclampsia", Ultrasound Obstet. Gynecol., 2009, 33:23-33 (2009).
Poon et al., "First-trimester prediction of hypertensive disorders in pregnancy," Hypertension, 2009 53:812-818.

(56) References Cited

OTHER PUBLICATIONS

Poon et al., "Hypertensive disorders in pregnancy: screening by biophysical and biochemical markers at 11-13 weeks," Ultrasound Obstet. Gynecol., 2010, 35:662-670.
Poon et al., "Inter-arm blood pressure differences in pregnant women," BJOG, 2008, 115:1122-1130.
Poon et al., "Maternal serum ADAM12 (A disintegrin and metalloprotease) in chromosomally abnormal pregnancy at 11-13 weeks," Am. J. Obstet, Gynecol., 2009, 200:508.e1-508.e6.
Poon et al., "Maternal serum placental growth factor (PlGF) in small for gestational age pregnancy at 11+0 to 13+6 weeks of gestation," Prenat. Diagn., 2008, 28:1110-1115.
Poon et al., "Mean Arterial Pressure at 11+0 to 13+6 Weeks in the Prediction of Preeclampsia", Hypertension, 2008, Part II, pp. 1027-1033.
Potter Clarkson LLP, Notice of Opposition by Beckman Coulter, Inc. received in EP Application No. 09704269.1 on Mar. 18, 2015, 26 pages.
Potter Clarkson LLP, Notice of Opposition by Siemens Healthcare Diagnostics Inc. received in EP Application No. 09704269.1 on Mar. 18, 2015, 24 pages.
Powers et al., "Soluble fms-like tyrosine kinase 1 (sFlt1), endoglin and placental growth factor (PlGF) in preeclampsia among high risk pregnancies", PLoS One, 2010, 5:10, e13263, 1-12.
Roberts et al., "Pathogenesis and genetics of pre-eclampsia," Lancet, 2001, 357:53-56.
Savvidou et al., "First trimester urinary placental growth factor and development of pre-eclampsia," BJOG, 2009, 116:643-647.
Sibai et al., "Risk factors associated with preeclampsia in healthy nulliparous women," Am. J. Obstet. Gynecol., 1997, 177:1003-1010.
Smith et al., "Circulating Angiogenic Factors in Early Pregnancy and the Risk of Preeclampsia, Intrauterine Growth Restriction, Spontaneous Preterm Birth, and Stillbirth," Obstetrics & Gynecology, 2007, 109:1316-1324.
Spencer et al., "First trimester maternal serum placenta growth factor (PlGF) concentrations in pregnancies with fetal trisomy 21 or trisomy 18," Prenat. Diagn., 2001, 21:718-722.
Spencer et al., "Low levels of maternal serum PAPP-A in the first trimester and the risk of pre-eclampsia," Prenatal Diagnosis, 2008, 28:7-1.
Spencer et al., "Prediction of pregnancy complications by first-trimester maternal serum PAPP-A and fee b-hCG and with second trimester uterine artery Doppler," Prenatal Diagnosis, 2005, 25:949-953.
Supplementary European Search Report; Application No. 09704269.1-1223 / 2245180; dated May 26, 2011; 1 page.
Swiss-Prot Entry P49763.2 (printout of Feb. 2, 2015).
Than et al., "Application of pregnancy-related proteins in prenatal and tumor diagnostics—a workshop report," Placenta, 2005, 26(Suppl A):S110-S113.
Than et al., "Prediction of preeclampsia—a workshop report," Placenta, 2008, 29(Suppl A):S83-S85.
Visser et al., The Fetal Medicine Foundation, Program of the 8th World Congress in Fetal Medicine, Portorose, Slovenia, Jun. 28-Jul. 2, 2009.
Yu et al., "Prediction of pre-eclampsia by uterine artery Doppler imaging: relationship to gestational age at delivery and small-for-gestational age," Ultrasound Obstet. Gynecol., 2008, 31:310-313.

* cited by examiner

Fig 7 Table 1

| combName | combType | gestArea | case | controls | cases | controlType | power | corr | combs | auc | fpr5 | fpr10 | fpr15 | fpr20 | fpr25 | fpr30 |
|---|---|---|---|---|---|---|---|---|---|---|---|---|---|---|---|
| Selectin.p2i0c1 | p2i0c1 | w10w13 | peAll | 37 | 65 | control | p2 | i0 | c1 | 0,56 | 0,12 | 0,14 | 0,20 | 0,29 | 0,37 | 0,40 |
| Plgf.Selectin.p2i1c2 | p2i1c2 | w10w13 | peAll | 37 | 65 | control | p2 | i1 | c2 | 0,58 | 0,06 | 0,09 | 0,11 | 0,23 | 0,37 | 0,42 |
| Plgf.p2i0c1 | p2i0c1 | w10w13 | peAll | 37 | 65 | control | p2 | i0 | c1 | 0,46 | 0,02 | 0,06 | 0,09 | 0,12 | 0,26 | 0,31 |
| Plgf.Selectin.p2i1c2 | p2i1c2 | w10w13 | peAllEarly | 37 | 20 | control | p2 | i1 | c1 | 0,68 | 0,10 | 0,10 | 0,20 | 0,25 | 0,60 | 0,60 |
| Selectin.p2i0c1 | p2i0c1 | w10w13 | peAllEarly | 37 | 20 | control | p2 | i0 | c1 | 0,60 | 0,05 | 0,10 | 0,10 | 0,35 | 0,40 | 0,40 |
| Plgf.p2i0c1 | p2i0c1 | w10w13 | peAllEarly | 37 | 20 | control | p2 | i0 | c1 | 0,61 | 0,00 | 0,05 | 0,30 | 0,40 | 0,40 | 0,45 |
| Plgf.Selectin.p2i1c2 | p2i1c2 | w10w13 | peChtn | 37 | 22 | control | p2 | i1 | c2 | 0,69 | 0,18 | 0,27 | 0,41 | 0,41 | 0,50 | 0,55 |
| Selectin.p2i0c1 | p2i0c1 | w10w13 | peChtn | 37 | 22 | control | p2 | i0 | c1 | 0,64 | 0,05 | 0,23 | 0,23 | 0,41 | 0,41 | 0,23 |
| Plgf.p2i0c1 | p2i0c1 | w10w13 | peChtn | 37 | 22 | control | p2 | i0 | c1 | 0,56 | 0,05 | 0,09 | 0,09 | 0,14 | 0,18 | 0,37 |
| Plgf.p2i0c1 | p2i0c1 | w10w13 | peWoChtn | 37 | 43 | control | p2 | i0 | c1 | 0,54 | 0,09 | 0,19 | 0,19 | 0,26 | 0,30 | 0,42 |
| Selectin.p2i0c1 | p2i0c1 | w10w13 | peWoChtn | 37 | 43 | control | p2 | i0 | c1 | 0,61 | 0,07 | 0,14 | 0,19 | 0,23 | 0,37 | 0,42 |
| Plgf.Selectin.p2i1c2 | p2i1c2 | w10w13 | peWoChtn | 37 | 43 | control | p2 | i1 | c2 | 0,64 | 0,07 | 0,12 | 0,16 | 0,26 | 0,26 | 0,49 |
| Plgf.Selectin.p2i1c2 | p2i1c2 | w18w22 | peAll | 87 | 166 | control | p2 | i1 | c2 | 0,60 | 0,20 | 0,25 | 0,28 | 0,35 | 0,38 | 0,43 |
| Plgf.p2i0c1 | p2i0c1 | w18w22 | peAll | 87 | 166 | control | p2 | i0 | c1 | 0,59 | 0,16 | 0,21 | 0,33 | 0,37 | 0,39 | 0,40 |
| Selectin.p2i0c1 | p2i0c1 | w18w22 | peAll | 87 | 166 | control | p2 | i0 | c1 | 0,49 | 0,05 | 0,11 | 0,14 | 0,19 | 0,22 | 0,25 |
| Plgf.Selectin.p2i1c2 | p2i1c2 | w18w22 | peAllEarly | 87 | 48 | control | p2 | i1 | c2 | 0,76 | 0,35 | 0,44 | 0,44 | 0,50 | 0,63 | 0,67 |
| Plgf.p2i0c1 | p2i0c1 | w18w22 | peAllEarly | 87 | 48 | control | p2 | i0 | c1 | 0,73 | 0,35 | 0,38 | 0,52 | 0,58 | 0,60 | 0,63 |
| Selectin.p2i0c1 | p2i0c1 | w18w22 | peAllEarly | 87 | 48 | control | p2 | i0 | c1 | 0,60 | 0,13 | 0,17 | 0,25 | 0,31 | 0,38 | 0,44 |
| Plgf.Selectin.p2i1c2 | p2i1c2 | w18w22 | peChtn | 87 | 46 | control | p2 | i1 | c2 | 0,65 | 0,28 | 0,33 | 0,35 | 0,39 | 0,46 | 0,48 |
| Selectin.p2i0c1 | p2i0c1 | w18w22 | peChtn | 87 | 46 | control | p2 | i0 | c1 | 0,60 | 0,15 | 0,26 | 0,26 | 0,33 | 0,35 | 0,50 |
| Plgf.p2i0c1 | p2i0c1 | w18w22 | peChtn | 87 | 46 | control | p2 | i0 | c1 | 0,62 | 0,15 | 0,20 | 0,28 | 0,35 | 0,37 | 0,39 |
| Plgf.Selectin.p2i1c2 | p2i1c2 | w18w22 | peWoChtn | 87 | 120 | control | p2 | i1 | c2 | 0,58 | 0,15 | 0,26 | 0,37 | 0,38 | 0,41 | 0,43 |
| Plgf.p2i0c1 | p2i0c1 | w18w22 | peWoChtn | 87 | 120 | control | p2 | i0 | c1 | 0,58 | 0,16 | 0,23 | 0,34 | 0,38 | 0,38 | 0,41 |
| Selectin.p2i0c1 | p2i0c1 | w18w22 | peWoChtn | 87 | 120 | control | p2 | i0 | c1 | 0,52 | 0,07 | 0,11 | 0,17 | 0,19 | 0,27 | 0,34 |
| Plgf.Selectin.p2i1c2 | p2i1c2 | w26w36 | peAll | 231 | 445 | control | p2 | i1 | c2 | 0,69 | 0,29 | 0,43 | 0,47 | 0,54 | 0,58 | 0,62 |

Fig 7 Table 1 continues

| | | | | | | | | | | | | | | | |
|---|---|---|---|---|---|---|---|---|---|---|---|---|---|---|---|
| Plgf.p2i0c1 | p2i0c1 | w26w36 | peAll | 231 | 445 | control | p2 | i0 | c1 | 0,69 | 0,29 | 0,41 | 0,48 | 0,55 | 0,58 | 0,61 |
| Selectin.p2i0c1 | p2i0c1 | w26w36 | peAll | 231 | 445 | control | p2 | i0 | c1 | 0,55 | 0,10 | 0,18 | 0,23 | 0,25 | 0,28 | 0,38 |
| Plgf.Selectin.p2i1c2 | p2i1c2 | w26w36 | peAllEarly | 231 | 107 | control | p2 | i1 | c2 | 0,85 | 0,64 | 0,72 | 0,73 | 0,76 | 0,77 | 0,79 |
| Plgf.p2i0c1 | p2i0c1 | w26w36 | peAllEarly | 231 | 107 | control | p2 | i0 | c1 | 0,84 | 0,62 | 0,70 | 0,74 | 0,77 | 0,79 | 0,79 |
| Selectin.p2i0c1 | p2i0c1 | w26w36 | peAllEarly | 231 | 107 | control | p2 | i0 | c1 | 0,58 | 0,14 | 0,19 | 0,25 | 0,28 | 0,31 | 0,40 |
| Plgf.p2i0c1 | p2i0c1 | w26w36 | peChtn | 231 | 116 | control | p2 | i0 | c1 | 0,63 | 0,23 | 0,33 | 0,42 | 0,47 | 0,50 | 0,53 |
| Plgf.Selectin.p2i1c2 | p2i1c2 | w26w36 | peChtn | 231 | 116 | control | p2 | i1 | c2 | 0,65 | 0,21 | 0,31 | 0,44 | 0,46 | 0,48 | 0,53 |
| Selectin.p2i0c1 | p2i0c1 | w26w36 | peChtn | 231 | 116 | control | p2 | i0 | c1 | 0,52 | 0,07 | 0,09 | 0,17 | 0,22 | 0,26 | 0,30 |
| Plgf.Selectin.p2i1c2 | p2i1c2 | w26w36 | peWoChtn | 231 | 329 | control | p2 | i1 | c2 | 0,72 | 0,31 | 0,47 | 0,51 | 0,56 | 0,61 | 0,64 |
| Plgf.p2i0c1 | p2i0c1 | w26w36 | peWoChtn | 231 | 329 | control | p2 | i0 | c1 | 0,72 | 0,31 | 0,44 | 0,50 | 0,58 | 0,61 | 0,64 |
| Selectin.p2i0c1 | p2i0c1 | w26w36 | peWoChtn | 231 | 329 | control | p2 | i0 | c1 | 0,57 | 0,11 | 0,19 | 0,24 | 0,26 | 0,29 | 0,38 |
| Plgf.Selectin.p2i1c2 | p2i1c2 | w14w16 | peAll | 27 | 71 | control | p2 | i1 | c2 | 0,66 | 0,37 | 0,42 | 0,49 | 0,49 | 0,49 | 0,54 |
| Plgf.p2i0c1 | p2i0c1 | w14w16 | peAll | 27 | 71 | control | p2 | i0 | c1 | 0,63 | 0,37 | 0,42 | 0,42 | 0,44 | 0,45 | 0,55 |
| Selectin.p2i0c1 | p2i0c1 | w14w16 | peAll | 27 | 71 | control | p2 | i0 | c1 | 0,49 | 0,01 | 0,07 | 0,10 | 0,18 | 0,25 | 0,32 |
| Plgf.Selectin.p2i1c2 | p2i1c2 | w14w16 | peAllEarly | 27 | 21 | control | p2 | i1 | c2 | 0,79 | 0,57 | 0,67 | 0,67 | 0,71 | 0,76 | 0,76 |
| Plgf.p2i0c1 | p2i0c1 | w14w16 | peAllEarly | 27 | 21 | control | p2 | i0 | c1 | 0,70 | 0,52 | 0,57 | 0,57 | 0,62 | 0,62 | 0,67 |
| Selectin.p2i0c1 | p2i0c1 | w14w16 | peAllEarly | 27 | 21 | control | p2 | i0 | c1 | 0,59 | 0,14 | 0,14 | 0,14 | 0,19 | 0,24 | 0,29 |
| Plgf.Selectin.p2i1c2 | p2i1c2 | w14w16 | peAllLate | 27 | 15 | control | p2 | i1 | c2 | 0,68 | 0,27 | 0,27 | 0,40 | 0,40 | 0,53 | 0,60 |
| Plgf.p2i0c1 | p2i0c1 | w14w16 | peAllLate | 27 | 15 | control | p2 | i0 | c1 | 0,62 | 0,27 | 0,27 | 0,33 | 0,40 | 0,40 | 0,47 |
| Selectin.p2i0c1 | p2i0c1 | w14w16 | peAllLate | 27 | 15 | control | p2 | i0 | c1 | 0,65 | 0,07 | 0,27 | 0,33 | 0,33 | 0,53 | 0,53 |
| Plgf.Selectin.p2i1c2 | p2i1c2 | w14w16 | peChtn | 27 | 19 | control | p2 | i1 | c2 | 0,80 | 0,42 | 0,42 | 0,47 | 0,47 | 0,58 | 0,68 |
| Plgf.p2i0c1 | p2i0c1 | w14w16 | peChtn | 27 | 19 | control | p2 | i0 | c1 | 0,76 | 0,42 | 0,42 | 0,47 | 0,58 | 0,58 | 0,63 |
| Selectin.p2i0c1 | p2i0c1 | w14w16 | peChtn | 27 | 19 | control | p2 | i0 | c1 | 0,63 | 0,05 | 0,11 | 0,21 | 0,47 | 0,47 | 0,63 |
| Plgf.Selectin.p2i1c2 | p2i1c2 | w14w16 | peChtnEarly | 27 | 6 | control | p2 | i1 | c2 | 1,00 | 1,00 | 1,00 | 1,00 | 1,00 | 1,00 | 1,00 |
| Plgf.p2i0c1 | p2i0c1 | w14w16 | peChtnEarly | 27 | 6 | control | p2 | i0 | c1 | 0,83 | 0,83 | 0,83 | 0,83 | 0,83 | 0,83 | 0,83 |
| Selectin.p2i0c1 | p2i0c1 | w14w16 | peChtnEarly | 27 | 6 | control | p2 | i0 | c1 | 0,67 | 0,33 | 0,33 | 0,33 | 0,33 | 0,33 | 0,33 |
| Plgf.Selectin.p2i1c2 | p2i1c2 | w14w16 | peChtnLate | 27 | 5 | control | p2 | i1 | c2 | 0,92 | 0,60 | 0,60 | 0,80 | 0,80 | 1,00 | 1,00 |
| Plgf.p2i0c1 | p2i0c1 | w14w16 | peChtnLate | 27 | 5 | control | p2 | i0 | c1 | 0,70 | 0,40 | 0,40 | 0,40 | 0,40 | 0,40 | 0,40 |

Fig 7 Table 1 continues

| | | | | | | | | | | | | | | | | |
|---|---|---|---|---|---|---|---|---|---|---|---|---|---|---|---|---|
| Selectin.p2i0c1 | p2i0c1 | w14w16 | peChtnLate | 27 | 5 | control | p2 | i0 | c1 | 0,73 | 0,40 | 0,40 | 0,60 | 0,60 | 0,60 | 0,60 |
| Plgf.Selectin.p2i1c2 | p2i1c2 | w14w16 | peWoChtn | 27 | 52 | control | p2 | i1 | c2 | 0,67 | 0,29 | 0,38 | 0,46 | 0,46 | 0,46 | 0,63 |
| Plgf.p2i0c1 | p2i0c1 | w14w16 | peWoChtn | 27 | 52 | control | p2 | i0 | c1 | 0,63 | 0,37 | 0,37 | 0,42 | 0,42 | 0,44 | 0,54 |
| Selectin.p2i0c1 | p2i0c1 | w14w16 | peWoChtn | 27 | 15 | control | p2 | i0 | c1 | 0,55 | 0,06 | 0,10 | 0,10 | 0,21 | 0,23 | 0,31 |
| Plgf.Selectin.p2i1c2 | p2i1c2 | w14w16 | peWoChtnEarly | 27 | 15 | control | p2 | i1 | c2 | 0,69 | 0,27 | 0,47 | 0,47 | 0,53 | 0,53 | 0,67 |
| Plgf.p2i0c1 | p2i0c1 | w14w16 | peWoChtnEarly | 27 | 15 | control | p2 | i0 | c1 | 0,65 | 0,40 | 0,47 | 0,47 | 0,53 | 0,53 | 0,60 |
| Selectin.p2i0c1 | p2i0c1 | w14w16 | peWoChtnEarly | 27 | 15 | control | p2 | i0 | c1 | 0,62 | 0,13 | 0,27 | 0,33 | 0,33 | 0,40 | 0,53 |
| Plgf.Selectin.p2i1c2 | p2i1c2 | w14w16 | peWoChtnLate | 27 | 10 | control | p2 | i1 | c2 | 0,63 | 0,20 | 0,20 | 0,20 | 0,40 | 0,50 | 0,50 |
| Plgf.p2i0c1 | p2i0c1 | w14w16 | peWoChtnLate | 27 | 10 | control | p2 | i0 | c1 | 0,58 | 0,20 | 0,20 | 0,30 | 0,40 | 0,40 | 0,50 |
| Selectin.p2i0c1 | p2i0c1 | w14w16 | peWoChtnLate | 27 | 10 | control | p2 | i0 | c1 | 0,59 | 0,10 | 0,10 | 0,20 | 0,20 | 0,20 | 0,50 |
| Plgf.Selectin.p2i1c2 | p2i1c2 | w29w33 | peAll | 91 | 200 | control | p2 | i1 | c2 | 0,71 | 0,29 | 0,43 | 0,49 | 0,57 | 0,60 | 0,64 |
| Plgf.p2i0c1 | p2i0c1 | w29w33 | peAll | 91 | 200 | control | p2 | i0 | c1 | 0,70 | 0,30 | 0,36 | 0,47 | 0,58 | 0,62 | 0,63 |
| Selectin.p2i0c1 | p2i0c1 | w29w33 | peAll | 91 | 200 | control | p2 | i0 | c1 | 0,59 | 0,14 | 0,21 | 0,23 | 0,31 | 0,35 | 0,43 |
| Plgf.Selectin.p2i1c2 | p2i1c2 | w29w33 | peAllEarly | 91 | 54 | control | p2 | i1 | c2 | 0,89 | 0,74 | 0,74 | 0,74 | 0,81 | 0,83 | 0,85 |
| Plgf.p2i0c1 | p2i0c1 | w29w33 | peAllEarly | 91 | 54 | control | p2 | i0 | c1 | 0,88 | 0,70 | 0,72 | 0,76 | 0,81 | 0,83 | 0,83 |
| Selectin.p2i0c1 | p2i0c1 | w29w33 | peAllEarly | 91 | 54 | control | p2 | i0 | c1 | 0,65 | 0,19 | 0,28 | 0,28 | 0,37 | 0,43 | 0,56 |
| Plgf.Selectin.p2i1c2 | p2i1c2 | w29w33 | peAllLate | 91 | 42 | control | p2 | i1 | c2 | 0,69 | 0,26 | 0,31 | 0,38 | 0,48 | 0,55 | 0,57 |
| Plgf.p2i0c1 | p2i0c1 | w29w33 | peAllLate | 91 | 42 | control | p2 | i0 | c1 | 0,67 | 0,21 | 0,31 | 0,40 | 0,55 | 0,60 | 0,60 |
| Selectin.p2i0c1 | p2i0c1 | w29w33 | peAllLate | 91 | 42 | control | p2 | i0 | c1 | 0,57 | 0,10 | 0,17 | 0,19 | 0,33 | 0,36 | 0,40 |
| Plgf.Selectin.p2i1c2 | p2i1c2 | w29w33 | peChtn | 91 | 52 | control | p2 | i1 | c2 | 0,66 | 0,25 | 0,29 | 0,46 | 0,52 | 0,54 | 0,58 |
| Plgf.p2i0c1 | p2i0c1 | w29w33 | peChtn | 91 | 52 | control | p2 | i0 | c1 | 0,65 | 0,23 | 0,27 | 0,42 | 0,50 | 0,56 | 0,56 |
| Selectin.p2i0c1 | p2i0c1 | w29w33 | peChtn | 91 | 52 | control | p2 | i0 | c1 | 0,46 | 0,02 | 0,12 | 0,13 | 0,21 | 0,21 | 0,25 |
| Plgf.Selectin.p2i1c2 | p2i1c2 | w29w33 | peChtnEarly | 91 | 18 | control | p2 | i1 | c2 | 0,76 | 0,56 | 0,56 | 0,56 | 0,56 | 0,61 | 0,61 |
| Plgf.p2i0c1 | p2i0c1 | w29w33 | peChtnEarly | 91 | 18 | control | p2 | i0 | c1 | 0,76 | 0,50 | 0,50 | 0,50 | 0,50 | 0,56 | 0,56 |
| Selectin.p2i0c1 | p2i0c1 | w29w33 | peChtnEarly | 91 | 18 | control | p2 | i0 | c1 | 0,69 | 0,17 | 0,28 | 0,28 | 0,44 | 0,44 | 0,67 |
| Plgf.Selectin.p2i1c2 | p2i1c2 | w29w33 | peChtnLate | 91 | 12 | control | p2 | i1 | c2 | 0,55 | 0,08 | 0,25 | 0,25 | 0,25 | 0,25 | 0,33 |
| Plgf.p2i0c1 | p2i0c1 | w29w33 | peChtnLate | 91 | 12 | control | p2 | i0 | c1 | 0,53 | 0,08 | 0,08 | 0,08 | 0,17 | 0,25 | 0,25 |
| Selectin.p2i0c1 | p2i0c1 | w29w33 | peChtnLate | 91 | 12 | control | p2 | i0 | c1 | 0,46 | 0,00 | 0,00 | 0,08 | 0,17 | 0,17 | 0,25 |

Fig 7 Table 1 continues

| | | | | | | | | | | | | | | | | | |
|---|---|---|---|---|---|---|---|---|---|---|---|---|---|---|---|---|---|
| Plgf.Selectin.p2i1c2 | p2i1c2 | w29w33 | peWoChtn | 91 | 148 | control | p2 | i1 | c2 | 0,73 | 0,31 | 0,45 | 0,49 | 0,60 | 0,60 | 0,64 |
| Plgf.p2i0c1 | p2i0c1 | w29w33 | peWoChtn | 91 | 148 | control | p2 | i0 | c1 | 0,72 | 0,32 | 0,39 | 0,48 | 0,61 | 0,63 | 0,65 |
| Selectin.p2i0c1 | p2i0c1 | w29w33 | peWoChtn | 91 | 148 | control | p2 | i0 | c1 | 0,60 | 0,16 | 0,23 | 0,24 | 0,32 | 0,37 | 0,45 |
| Plgf.Selectin.p2i1c2 | p2i1c2 | w29w33 | peWoChtnEarly | 91 | 36 | control | p2 | i1 | c2 | 0,95 | 0,78 | 0,83 | 0,86 | 0,94 | 0,94 | 0,97 |
| Plgf.p2i0c1 | p2i0c1 | w29w33 | peWoChtnEarly | 91 | 36 | control | p2 | i0 | c1 | 0,95 | 0,81 | 0,83 | 0,89 | 0,94 | 0,94 | 0,94 |
| Selectin.p2i0c1 | p2i0c1 | w29w33 | peWoChtnEarly | 91 | 36 | control | p2 | i0 | c1 | 0,62 | 0,19 | 0,28 | 0,28 | 0,33 | 0,42 | 0,50 |
| Plgf.p2i0c1 | p2i0c1 | w29w33 | peWoChtnLate | 91 | 30 | control | p2 | i0 | c1 | 0,71 | 0,23 | 0,37 | 0,47 | 0,63 | 0,70 | 0,70 |
| Plgf.Selectin.p2i1c2 | p2i1c2 | w29w33 | peWoChtnLate | 91 | 30 | control | p2 | i1 | c2 | 0,76 | 0,27 | 0,33 | 0,47 | 0,57 | 0,57 | 0,73 |
| Selectin.p2i0c1 | p2i0c1 | w29w33 | peWoChtnLate | 91 | 30 | control | p2 | i0 | c1 | 0,61 | 0,13 | 0,23 | 0,27 | 0,37 | 0,40 | 0,43 |
| Plgf.Selectin.p2i1c2 | p2i1c2 | w10w13 | peAll | 145 | 65 | allControl | p2 | i1 | c2 | 0,59 | 0,06 | 0,09 | 0,18 | 0,26 | 0,32 | 0,40 |
| Plgf.p2i0c1 | p2i0c1 | w10w13 | peAll | 145 | 65 | allControl | p2 | i0 | c1 | 0,55 | 0,06 | 0,14 | 0,20 | 0,25 | 0,32 | 0,37 |
| Selectin.p2i0c1 | p2i0c1 | w10w13 | peAll | 145 | 65 | allControl | p2 | i0 | c1 | 0,51 | 0,11 | 0,14 | 0,15 | 0,20 | 0,22 | 0,26 |
| Plgf.Selectin.p2i1c2 | p2i1c2 | w10w13 | peChtn | 145 | 22 | allControl | p2 | i1 | c2 | 0,67 | 0,05 | 0,23 | 0,27 | 0,50 | 0,55 | 0,55 |
| Plgf.p2i0c1 | p2i0c1 | w10w13 | peChtn | 145 | 22 | allControl | p2 | i0 | c1 | 0,58 | 0,05 | 0,05 | 0,09 | 0,18 | 0,32 | 0,41 |
| Selectin.p2i0c1 | p2i0c1 | w10w13 | peChtn | 145 | 22 | allControl | p2 | i0 | c1 | 0,62 | 0,05 | 0,18 | 0,36 | 0,41 | 0,50 | 0,55 |
| Plgf.Selectin.p2i1c2 | p2i1c2 | w10w13 | peWoChtn | 145 | 43 | allControl | p2 | i1 | c2 | 0,64 | 0,09 | 0,16 | 0,30 | 0,37 | 0,40 | 0,49 |
| Plgf.p2i0c1 | p2i0c1 | w10w13 | peWoChtn | 145 | 43 | allControl | p2 | i0 | c1 | 0,58 | 0,12 | 0,21 | 0,28 | 0,30 | 0,37 | 0,40 |
| Selectin.p2i0c1 | p2i0c1 | w10w13 | peWoChtn | 145 | 43 | allControl | p2 | i0 | c1 | 0,59 | 0,07 | 0,16 | 0,23 | 0,28 | 0,30 | 0,35 |

METHOD FOR DETERMINING RISK OF PRE-ECLAMPSIA

PRIORITY

This application is a U.S national application of PCT-application PCT/FI2015/050566 filed on Sep. 1, 2015 and claiming priority of Finnish national application FI20145762 filed on Sep. 2, 2014, the contents of all of which are incorporated herein by reference.

Pre-eclampsia (PE) affects about 3 to 5% of pregnancies and is an important cause of maternal and perinatal mortality and morbidity. As reviewed by Perni et al., Hypertension. 2012; 59: 740-746 pre-eclampsia may also develop in women with chronic (preexisting) hypertension and it occurs 3 to 5 times more frequently compared with women who are normotensive at conception. The diagnosis of superimposed pre-eclampsia is often difficult, because women already have hypertension and some even have proteinuria. The pathogenesis of PE, as well as superimposed pre-eclampsia, is likely to involve placental vascular remodeling, leading to defective placentation, placental ischemia, and maternal endothelial cell dysfunction. Emerging data suggest that placental ischemia is associated with increased production of placental proteins, which, on release into the maternal circulation, cause maternal systemic inflammation and endothelial cell dysfunction. Superimposed PE is associated with even greater maternal and fetal morbidity and mortality than PE in women without preexisting hypertension Perni et al (2012).

Many biological markers present in maternal samples are currently recognized as associated with pre-eclampsia. Placental growth factor (PlGF) has been shown to be a good marker to predict pre-eclampsia (EP2368119A1), in particular early-onset pre-eclampsia (Pool et al. 2013, Vol. 33, No. 1, 2013 Issue release date: January 2013 Fetal Diagn Ther 2013; 33:16-27). However, it has turned out in the studies leading to this disclosure that it is not a good marker for those women, who have chronic hypertension.

There is thus a need for methods providing an early estimate on the risk for a pregnant individual having chronic hypertension for developing pre-eclampsia, in particular early or late onset pre-eclampsia.

Further, there is a need for a method for determining the risk based on an analysis of a biological sample, which can be performed in vitro.

Further, there is a need for a method for determining the risk based on an analysis of a biological sample, which can be performed during the first trimester of pregnancy.

Yet, there still is a need for a method for determining the risk of pre-eclampsia, in particular early or late onset pre-eclampsia, said method having improved detection rate in a single screen.

SUMMARY OF THE INVENTION

The present description provides methods useful for determining the risk that a pregnant individual having chronic hypertension will develop early pre-eclampsia or late pre-eclampsia. Useful combinations of biochemical markers and related clinical population studies are described herein. Additionally, it is proposed herein that certain sets of biochemical markers can be used to determine risk of early pre-eclampsia or late pre-eclampsia in a single screen. Surprisingly it has been found that the combination of PlGF and sP-selectin is useful for determining the risk of early and late pre-eclampsia of a pregnant individual having chronic hypertension.

Provided herein is a method for determining the risk of early or late onset pre-eclampsia in a pregnant individual, involving determining the levels of biochemical markers including PlGF and sP-selectin in one or more blood samples from the individual having chronic hypertension; and determining the risk of early or late onset pre-eclampsia using the determined levels of biochemical markers.

This method includes hypertension history of the individual; an individual having chronic hypertension and determining the risk of pre-eclampsia using the levels of the biochemical markers including PlGF and sP-selectin.

In the following text, the method provided herein will be further described with the aid of a detailed description and with reference to example 1.

BRIEF DESCRIPTION OF THE DRAWINGS

FIG. 7 Table 1

DETAILED DESCRIPTION OF THE INVENTION

Figure 1A:
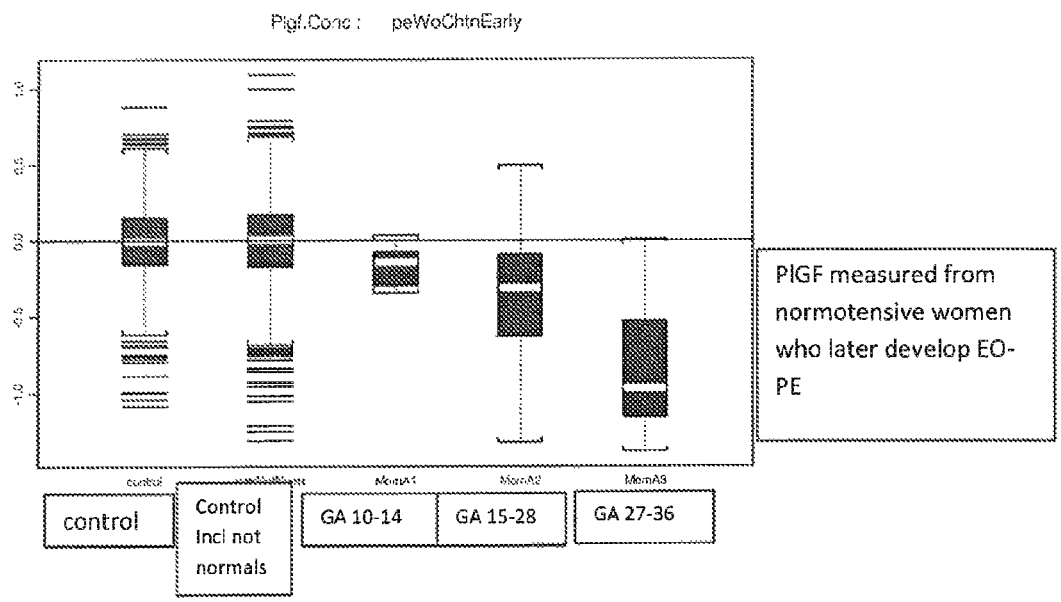
FIG. 1a shows PlGF measured from normotensive women who later develop EO-PE.

By chronic hypertension is meant a condition where the blood pressure of an individual is higher than normal over a long time. Usually high blood pressure is said to be present if it is often at or above 140/90 mmHg. Pregnant individual having chronic hypertension have suffered of hypertension already before pregnancy or a pregnant individual is diagnosed with it generally before 20 weeks gestation.

By superimposed pre-eclampsia is meant hypertension with or without proteinuria (AGOG Guidelines) in a woman with hypertension before 20 weeks of gestation. It can be characterized by:

- A sudden increase in proteinuria if already present in early gestation
- A sudden increase in hypertension
- The development of HELLP syndrome (HELLP syndrome is a group of symptoms that occur in pregnant women who have hemolysis, elevated liver enzymes and low platelet count).
- Women with chronic hypertension who develop headache, scotomata or epigastric pain.

Sample

The methods for determining the risk of an early or late pre-eclampsia in a pregnant individual involve using a biological sample from the pregnant individual. The biological sample can be any body fluid or tissue sample that contains the selected biochemical markers. Preferably the sample is blood or a fraction of blood, such as serum. The choice of biological sample can often depend on the assay formats available in a particular clinical laboratory for testing levels of markers. For example, some assay formats lack sensitivity needed for assaying whole blood, such that a clinical laboratory opts for testing a fraction of blood, such as serum, or using dried blood. Further, samples that have been preserved, such as by freezing or drying (e.g. on blood card format), are suitable for use in the methods described herein. Example 1 describes use of maternal blood in the form of serum. Exemplary biological samples useful for the methods described herein include blood, purified blood products (such as serum, plasma, etc.), urine, amniotic fluid, a chorionic villus biopsy, a placental biopsy and cervico-vaginal fluid. Preferable samples comprise blood samples. This means that the method is carried out in vitro, outside the body of the pregnant woman (also referred to herein as the mother, individual, patient or subject).

Typical assay formats for determining the level of polypeptide and other biomarkers in a sample involve use of a control polypeptide, especially when quantitating levels of such polypeptides. Commercially available proteins and other biomarkers can be used as standards in assays measuring the level of biochemical markers. Alternatively, methods for expressing proteins, such as in prokaryotic and eukaryotic systems and for synthesizing polypeptides are well known. Full length proteins and fragments thereof can be used as standards for quantitative determination of levels of biomarkers in a sample obtained from a pregnant woman.

By "a control sample" is here meant a sample obtained from a subject being at the same trimester or gestational age of pregnancy, and wherein the pregnancy is confirmed to have a specific outcome in respect to pre-eclampsia. Typically a "control sample" has been confirmed to have not developed pre-eclampsia (see Examples herein), although use of a control sample confirmed to have developed pre-eclampsia is possible. The term is here defined to encompass one or more samples, so that a control sample can be a set of samples obtained from a population. The pregnant controls chosen can be matched to the pre-eclampsia cases by biophysical parameters, such as maternal age, body mass index, ethnicity and gestational age, smoking status.

Level of Biochemical Markers

By "determining the levels of biochemical markers including PlGF and sP-selectin in at least one blood sample from the individual" means that a selected biochemical marker is determined by a method specifically assessing the level of the mentioned marker in a sample obtained from the pregnant woman and from a control sample. The level of a biochemical markers present in a sample can be determined using any assay format suitable for measuring proteins in biological samples. A common assay format for this purpose is the immunoassay, including, for example, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); dissociation-enhanced lanthanide fluorescent immunoassay (DELFIA) and chemiluminescence assays (CL).

A difference in the level of the biochemical marker in the sample relative to control sample indicates the risk of a pre-eclampsia in the woman. The difference can be an increase or decrease in the level of the biochemical marker, depending on the particular biomarker tested.

In certain circumstances, biological samples can be collected on more than one occasion from a pregnant woman, for example, when her hypertensive and/or placental condition requires monitoring for development of pre-eclampsia due to a priori risk, presentation of symptoms and/or other factors. The methods for determining risk of pre-eclampsia described herein can also be used for monitoring a pregnant individual who is undergoing a therapy or treatment for a hypertensive and/or placental condition. If desired, testing of biochemical and/or biophysical markers can be carried out in a home setting, such as by using dipstick biochemical test formats and automated blood pressure machines for home use.

By "an increased risk of developing an early or late onset pre-eclampsia" is meant that the likelihood of the subject (pregnant woman) for developing an early or late onset pre-eclampsia respectively, is on a level, which is higher than in a control group of pregnant women not developing said disorders.

Biochemical Markers

Most interesting biochemical markers in the context of determining the risk of pre-eclampsia in pregnant individuals are PlGF and sP-selectin.

Previously published studies have shown that a lowered level of PlGF indicates the development of pre-eclampsia.

The abbreviation "PlGF" means placenta growth factor. PlGF was originally cloned from human term placenta cDNA library in 1991. PlGF has been detected also in other tissues such as heart, lung, muscle and adipose tissue. PlGF belongs to the vascular endothelial growth factor (VEGF) family of proteins. It has a moderate sequence similarity of about 50% to VEGF-A. Alternative splicing generates four isoforms differing in size of which PlGF-1 and PlGF-2 are believed to be the major isoforms. PlGF-1 contains 131 amino acids (MW MONOMER 14.7 kDa, dimer 29.4 kDa). PlGF-2 contains PlGF-1 and of 21 amino acid heparin binding site insertion (MW monomer 17.3 kDa, dimer 34.6 kDa). The length of the full length PlGF-2 protein is thus 152 amino acids. PlGF-3 contains PlGF-1 and 72 amino acid insertion near the C-terminus (MW=monomer 22.8 kDa, dimer 45.6 kDa). Hence, the length of the full length PlGF-3 protein is 203 amino acids. PlGF-4 contains PlGF-3 and 21 amino acid heparin binding site insertion (MW=monomer 26.2 kDa, dimer 52.4 kDa). The length of the full length PlGF-4 is thus 224 amino acids. A reference to PlGF in this text without any definition of the isoform, means PlGF-1.

sP-selectin (also called P-selectin) is an adhesion molecule found in platelets. In inflammatory and thrombogenic conditions the molecule is expressed on the cell membrane and initiates interactions between endothelial cells, leukocytes and platelets. Platelet activation occurs in normal pregnancy, but this is exaggerated in PE which is characterized by platelet aggregation, vasoconstriction and endothelial injury. The factors controlling platelet activation are unknown but cytokines such as tumor necrosis factor α (TNF-α) have been implicated. The serum concentration of sP-selectin, a marker for platelet activation, is increased during established PE and there is also evidence that this elevation may be evident from the first-trimester of pregnancy (Akolekar R., et al. Maternal plasma P-selectin at 11 to 13 weeks of gestation in hypertensive disorders of pregnancy. Hypertens Pregnancy 2011; 30(3):311-21.

As is described herein, it has now been recognized that measurement of a combination of PlGF and sP-selectin in a maternal sample of a pregnant individual having chronic hypertension can be used to better determine risk of a pregnant woman developing early or late pre-eclampsia. The screening performance will thus be improved, as reflected by increased detection rates and lower false positive rates, relative to laboratory tests that employ only PlGF detection.

The selective detection of the markers PlGF and sP-selectin, can be combined with any other suitable biochemical markers or other indicators used for assessing the risk of developing pre-eclampsia. Such biochemical markers are for example those selected from Activin A, Ue-3, PAPP-A, PAI-1, PAI-2, PlGF-2, PlGF-3, PlGF-4, PP13, VEGF165b and ADAM-12.

Biophysical Markers

The methods described herein involve determining blood pressure of an individual. One or more measures selected from of systolic blood pressure, diastolic blood pressure and mean arterial blood pressure of the pregnant individual can be used.

The selective detection of the biochemical markers PlGF and sP-selectin can be combined also with any suitable biophysical markers for assessing the risk of developing pre-eclampsia. Such biochemical markers are for example blood pressure, mean arterial pressure (MAP) and uterine artery pulsatility index (PI). When applying this embodiment, determining the risk of developing pre-eclampsia is conducted using both the levels of the biochemical markers and the at least one biophysical marker.

Mean arterial pressure (MAP) refers to the average blood pressure over a cardiac cycle and is determined by the cardiac output (CO), systemic vascular resistance (SVR), and central venous pressure (CVP), using established procedures. A health care provider can use any method to measure the blood pressure of the pregnant individual, including, for example, palpation methods, auscultatory methods and oscillometric methods. Automated blood pressure measuring equipment also can be used.

In an embodiment, the methods described herein can involve determining uterine artery pulsatility index (PI). By "uterine artery pulsatility index" is meant an arterial blood-flow velocity waveform index designed to quantify the pulsatility or oscillations of the waveform. The PI has been found particularly useful in clinical cases in which there is diastolic flow reversal, i.e. bidirectional flow. The PI of the pregnant individual can be measured using any known method.

Maternal History

As used herein, "maternal history factors" refers to set of maternal characteristics expected to have impact on the biochemical and biophysical marker levels measured. In the field of adverse pregnancy outcome screening, maternal history is generally accepted to comprise at least maternal age, weeks of gestation, racial origin, cigarette smoking during pregnancy, method of conception, medical history, medication, parity, obstetric history and BMI. Also included may be the history of hypertension of the pregnant individual. To improve reliability of risk calculations, these factors can be included into algorithms. Inclusion of maternal history improves the detection rates of screens during pregnancy. To determine the factors usable in algorithms, maternal history is collected from a population from which relation of a biochemical marker and adverse pregnancy outcomes is determined. Collection is typically based on a questionnaire completed by the individual herself, which is preferably reviewed by a health-care professional together with the patient. When assessing the risk for an individual, same characteristics are collected from her and taken into account when performing the risk determination. Characteristics to be studied are hypertension history, maternal age, racial origin, cigarette smoking during pregnancy, method of conception, medical history, medication, parity, obstetric history and family history of PE in the mother. The collected or measured maternal weight and height can be converted into body mass index (BMI) in $Kg/m^2$.

Statistical Analysis

The Example below includes descriptions of statistical analysis of clinical studies relating to use of biomarkers to determine risk of maternal health conditions. The risk that a pregnant individual develops pre-eclampsia can be determined from biochemical marker levels using statistical analysis based on clinical data collected in a patient population study. There are multiple statistical methods for combining parameters that characterize the pregnant individual, such as levels of biochemical markers, to obtain a risk estimate. The likelihood method (Palomaki and Haddow, Am. J. Obstet. Gynecol. 156, 460-3 (1987)), the linear discriminant function method (Norgarrd-Pedersen et al. Clin. Genet. 37, 35-43 (1990)) and multiple logistic regression analysis are commonly used for this purpose. As such, the methods described herein for determining risk can be based on use of well-known statistical methods, in which a cut-off or a MoM is used to determine risk. It is understood that equivalent well-known statistical approaches can be taken to assess risks of medical conditions.

The basic principle of the likelihood method is that the population distributions for a parameter (such as the level of a biochemical marker) are known for the 'unaffected' and 'affected' groups. Thus, for any given parameter (such as level of marker and blood pressure reading), the likelihood of membership of the 'unaffected' and 'affected' groups can be calculated. The likelihood is calculated as the Gaussian height for the parameter based on the population mean and standard deviation. The 'likelihood ratio' is the ratio of the heights calculated using 'unaffected' and 'affected' population parameters, and is an expression of the increased risk of having a disorder, with respect to a prior risk.

A woman's prior odds (which is a statistical expression related to prior risk, as is described herein below) for having a maternal health condition can be calculated, for example, using a formula derived by clinical population studies (Cuckle et al. 1987). These prior odds can be modified using the likelihood ratio to derive the posterior odds that can be used for the pre-eclampsia or chromosomal abnormality risk estimate. A detailed description of use of the likelihood method for predicting risk that a fetus has a chromosomal abnormality is set forth, for example, in "Screening for Down's Syndrome," ed. J. G. Grudzinskas, T. Chard, M. Chapman and H. Cuckle; Published by Cambridge University Press, 1994). It is also possible to use observed distributions of likelihood ratios for determining risk using the methods described herein (see, for example, Spencer et al. Ann. Clin. Biochem., 29, 506-18 (1992)).

As an example of an approach for determining a risk that a pregnant woman develops pre-eclampsia, samples can be collected from a population of women known to have had pre-eclampsia. These samples are analyzed to determine the level of each biochemical marker. The determined level of each biochemical marker would typically then be converted to a multiple of the expected normal median (MoM) specific to a pregnancy of the same, gestational age, maternal weight, ethnicity, smoking status, method of conception and parity. Well known statistical regression approaches would then be used for risk calculations (see, for example Draper et al. Applied Regression Analysis (3th ed.) Wiley: New York, N.Y., 1998 and Cuckle H S et al., Estimating a woman's risk of having a pregnancy associated with Down's syndrome using her age and serum alphafetoprotein level. Br. J Obstet Gynecol 1987; 94:387-402; and other references above).

Pre-eclampsia and other Hypertensive Disorders

Pre-eclampsia and other hypertensive disorders occurring during pregnancy, as understood herein, are characterized by symptoms detectable when disorder has developed. If arranged in order of increasing severity, the least severe disorder is gestational hypertension. When in addition to gestational hypertension there is detected proteinuria, it is referred to as pre-eclampsia, which is divided into late and early onset pre-eclampsia as defined below. Early onset pre-eclampsia is the most severe of these disorders.

According to guidelines of the International Society for the Study of Hypertension in Pregnancy (Davey et al., Am. J. Obstet Gynecol; 158; 892098, 1988), Gestational hypertension is described as two recordings of diastolic blood pressure of 90 mmHg or higher at least 4 h apart, and severe hypertension as pressure of at least 110 mm Hg or higher at least 4 h apart or one recording of diastolic blood pressure of at least 120 mm Hg.

As used herein, the term "pre-eclampsia" means a disorder of pregnancy characterized in part by gestational hypertension and proteinuria. For previously normotensive women, PE is typically defined as gestational hypertension with proteinuria, and severe PE is typically defined as severe gestational hypertension with proteinuria. For women with chronic hypertension, superimposed PE is typically defined as the new development of proteinuria. Aspects of PE useful for making a diagnosis of PE can be classified according to guidelines set out by various medical organizations.

Proteinuria is often described as excretion of 300 mg or more in 24 h or two readings of 2+ or higher on dipstick analysis of midstream or catheter urine specimens if no 24 h collection was available. Women are classified as previously normotensive or with chronic hypertension generally before 20 weeks gestation.

Pre-eclampsia is understood and shall be defined herein to encompass and reside within a spectrum of pre-eclampsia disorders, including placental insufficiency, intrauterine growth retardation, early miscarriage, preterm birth, intrauterine death and eclampsia. Although not wishing to be bound by theory, it has been proposed that intrauterine growth retardation reflects an adaptation of the pregnant woman's body to cope with the condition of pre-eclampsia, which allows the fetus to survive. Early miscarriage and preterm birth, on the other hand, can reflect adaptation of the pregnant woman's body to cope with the condition of pre-eclampsia, which allow the woman to survive. In this context, intrauterine death would be a failure of this adaptation. Thus, the methods described herein for determining risk of pre-eclampsia include, and can also be used to determine risk of pre-eclampsia disorders on the pre-eclampsia spectrum.

Pre-eclampsia can develop as early as 20 weeks of gestation and is generally considered "early pre-eclampsia" or "early onset pre-eclampsia" if the delivery of a baby is done before week 34 because of pre-eclampsia. As used herein, "late pre-eclampsia" or "late onset pre-eclampsia" is defined so that delivery of a baby happens at or after week 34. Early pre-eclampsia is associated with increased morbidity and thus is considered a more severe form of pre-eclampsia. The methods for determining the risk of pre-eclampsia described herein are particularly useful for screening for "early pre-eclampsia." For use in the methods for detecting pre-eclampsia, a sample can be collected within first trimester, within second trimester and within third trimester. Preferably sample is collected within first or second trimester, preferably on first trimester. Although earlier testing is often a beneficial policy from a public health perspective, it is understood that collection of samples can sometimes be affected by practical considerations such as a woman delaying a visit to her health care provider until relatively later weeks of gestation.

In instances where a pregnant individual is determined to have an increased risk of developing pre-eclampsia using a method as described herein, the individual can receive therapy or lifestyle advice from a health care provider. Although there is no widely used treatment for pre-eclampsia, various studies have shown the benefit of therapies such as anti-hypertensive drugs, such as magnesium sulphate, aspirin, diazepam, and phenytoin; and dietary supplements, such as vitamin D, calcium, and selenium.

Timing of the Determination of Biochemical Marker Levels

The determination of the biochemical markers can be carried out during the first trimester or the second trimester of the pregnancy, or during both of the trimesters. However, the ability to detect a high risk of developing a hypertensive disorder within the first 12 weeks of pregnancy provides more time for a health care provider to provide prevention strategies for the pregnant woman. It is often desirable to complete a risk assessment early in pregnancy, to allow time for measures for preventing or retarding the pre-eclampsia to develop in the pregnant woman.

The methods described herein for determining the risk of a pregnant woman having chronic hypertension developing early or late pre-eclampsia can be practised using a sample obtained from the woman during the first trimester of pregnancy. In a specific embodiment, the sample is obtained during first trimester of pregnancy, preferably during weeks 8-13, more preferably during weeks 11-13, of gestational age. In an embodiment, one or more samples can be obtained from the woman at one or more trimesters of pregnancy. According to another embodiment of the present method, the sample is taken during the second trimester of the pregnancy. Typically this means the weeks 14 to 26 of the pregnancy.

Optionally, one sample can be obtained during the first trimester and another in a later stage of pregnancy, preferably during the second trimester of the pregnancy. The ability to detect a high risk of developing pre-eclampsia within the first trimester of pregnancy provides more time for a health care provider to provide prevention strategies for the pregnant woman. It is often desirable to complete a risk assessment early in pregnancy, to allow time for measures for preventing or retarding the PE condition to develop in the woman.

Computation of Risks

Typically, results obtained from measurement of levels of biochemical markers are processed using algorithms run on a computer. A computer program which when executed on a computer causes the computer to perform a process for determining risk of pre-eclampsia in a pregnant woman. The process can involve inputting a measurement of at least two biomarkers obtained by: i) assaying a sample obtained from the pregnant woman, wherein at least said biochemical markers comprise at least PlGF and sP-selectin; ii) comparing the level of each biomarker in the sample with the level of the same biomarker in a control sample, wherein a differences in levels of biochemical markers in the sample relative to the control sample are indicative of pre-eclampsia, and iii) determining a quantitative estimate of said risk based on the result of the comparing.

In addition the method may involve the use of maternal hypertension history in order select the individuals having chronic hypertension.

The computer program can further involve use of at least one additional biochemical marker. Optionally the computer program can further involve use of at least one additional biochemical marker selected from the group comprising Activin A, Ue-3, PAPP-A, PAI-1, PAI-2, PlGF-2, PlGF-3, VEGF165b, PlGF-4, and ADAM-12.

The computer program can involve inputting a measurement of at least one biomarker obtained by determining one or more biophysical markers of the subject; comparing the one or more biophysical markers of the subject with the same biophysical marker in a control subject, wherein an increased or decreased measure of the one or more biophysical marker in the subject relative to the control is indicative of an increased risk of developing pre-eclampsia, and determining a quantitative estimate of risk of developing pre-eclampsia based on the result of the compared one of more biochemical marker and the compared one or more biophysical marker.

In the computer program, the process can also include determining the quantitative estimate of risk of pre-eclampsia comprises determining the likelihood of a pre-eclampsia using a multivariate analysis, and wherein the multivariate analysis comprises using levels of the biochemical markers and distribution parameters derived from a set of control reference data. Preferably, the multivariate analysis is a multivariate Gaussian analysis.

Kit for Assessing Risk of Pre-eclampsia in a Pregnant Woman

The method described herein can be employed using kits or commercial packages for assessing risk of pre-eclampsia in a pregnant woman having chronic hypertension.

According to one embodiment, the method is employed using at least two kits, one for PlGF, and another for sP-selectin. Each kit contains at least two binding partners binding specifically to the marker (e.g. PlGF) and at least one of the binding partners is detectable.

According to another embodiment, the kit provides i) at least four detectable binding partners, wherein at least two detectable binding partners bind specifically to PlGF and at least two detectable binding partners bind specifically to sP-selectin. At least one of binding partners for each marker is detectable.

In embodiments, the detectable binding partner is an antibody or antigen-binding fragment thereof.

In a further specific embodiment, a kit can further provide instructions for using the detectable binding partners in the determination. Reagent volumes, incubation times, reaction conditions etc. can be provided in the instructions.

Detection Method

Herein is provided, in one aspect, a method for determining the risk of a pregnant woman developing pre-eclampsia. The method involves determining the level of at least two biochemical markers in a sample obtained from a pregnant woman, wherein said biochemical markers comprise PlGF and sP-selectin; and determining the risk of pre-eclampsia using the determined levels of biochemical markers. Preferably said pre-eclampsia for which the risk is determined, is early onset pre-eclampsia.

In an embodiment of the method, determining the risk of a pregnant woman developing pre-eclampsia, further comprises using maternal history factors, in particular the history of hypentension.

According to the disclosure of the method, decreased level of PlGF and increased level of sP-selectin in a sample obtained from a subject are indicative of increased risk of early or late onset pre-eclampsia in said subject.

Observations on Samples

In other words, at least one of the following observations, thus differences in levels, are identified: the level of PlGF in a sample obtained from a subject is decreased relative to the level of PlGF in the control sample; the level of sP-selectin in a sample obtained from a subject is increased relative to the level of sP-selectin in the control sample.

These observations are generated into numerical values, which in an algorithm produce an estimate for the risk of a pregnant woman developing early or late onset pre-eclampsia.

Briefly, an exemplary version of a method as described herein for determining risk of early or late pre-eclampsia of a pregnant woman with chronic hypertension can be performed by taking a blood sample from the pregnant woman. The blood can be processed to prepare plasma or serum if desired. Assay for a biochemical marker would be carried out using a standard immunoassay using at least two antibodies (one coated on the microtiter plate, capture Ab, and another labeled with a detectable label, tracer Ab) specific for a biochemical marker, PlGF and sP-selectin. An example is use of an enzyme linked immunosorbent assay (ELISA) in which intensity of color development in a test sample is proportional to the concentration of marker present. Based on this test, the level of the biochemical marker can be calculated. This level can be used in a risk algorithm independently, or in combination with levels of other markers, if desired. To design the risk algorithm, standard logistic regression analysis of a data set adjusted on the assumption of % prevalence of pre-eclampsia in the population can be used. To determine whether the level of biochemical markers is greater than or less than normal, the normal level of biochemical marker present in a maternal biological sample from a relevant population is determined. The relevant population can be defined based on any characteristics than can affect normal (unaffected) levels of the markers. For determining risk of early pre-eclampsia, the relevant population can be established on the basis of low risk for early pre-eclampsia, and for late onset pre-eclampsia respectively. Once the normal marker levels are known, the determined marker levels can be compared and the significance of the difference determined using standard statistical methods. When there is a statistically significant difference between the determined marker level and the normal level, there is a significant risk that the tested individual will develop an early or late onset pre-eclampsia.

The level of the selected biochemical marker in the sample is compared with the level of the same biochemical marker in a control sample. A difference in the level of biochemical marker in the sample relative to the control sample is indicative of an increased risk of developing earlier late onset pre-eclampsia. By a difference is meant a statistically significant difference in the values. By the presence of "increased or decreased levels" of any of the biochemical markers means that the level of any of the biochemical marker deviates statistically significantly from the level of the same biochemical marker in a control sample being higher or lower than the level in the control sample.

To analyze the measurement results of a single sample in routine screening for pre-eclampsia, data of a control population is first needed. This data is obtained by measuring the selected biochemical markers from a large number of samples, preferably more than 100 samples per each week of pregnancy. The measured concentrations of the selected biochemical markers are then preferably $\log_{10}$ transformed to make the distribution of the biological variation Gaussian. Subsequently, a median concentration and standard deviation for each selected biochemical marker is determined for each pregnancy week from the control data. Afterwards, the results of any single sample can be compared to the appropriate median concentrations to determine whether the concentrations of the selected biochemical markers differ from their normal values. This comparison can be used as a basis of calculating the patient risk for pre-eclampsia as a basis of making a diagnosis early or late onset pre-eclampsia. An example of such data resulting from studies conducted in the examples.

Matched case-control studies can also be made to demonstrate the behaviour of biochemical markers PlGF and sP-selectin. In such studies, a control population that is matched by physiological parameters to the early or late onset pre-eclampsia case population is used. Slightly different methods can also be used to calculate the results of such study as compared to routine screening.

Combination of PlGF, measurement and the present method for determining the risk of a pregnant woman with chronic hypertension developing an early or late onset pre-eclampsia.

As one embodiment, of the method for determining the risk of a pregnant woman having chronic hypertension developing an early or late onset pre-eclampsia involves measuring the difference in the level of PlGF, which has been earlier been reported to be indicative of pre-eclampsia and combining the measuring it with sP-selectin to said analysis. PlGF predicts better PE without chronic hypertension compared to sP-selectin, whereas sP-selectin predicts better PE with chronic hypertension than PlGF. The combination of PlGF and sP-selectin predicts all forms of PE. With the present method using a biomarker combination PlGF and sP-selectin, those showing a risk for developing early pre-eclampsia, or late onset pre-eclampsia, can be monitored and treated in a manner suitable for said conditions.

PlGF alone is a poor marker to predict superimposed EO-PE. When used in combination with sP-Selectin performance increases remarkably. Marker combination detects about 60% of cases at 10% FPR when measured during the $1^{st}$ trimester of pregnancy while PlGF alone detects only about 20% of those women who will develop superimposed EO-PE.

PlGF used alone detects about 40% of the LO-PE (late onset PE) cases, while PlGF together with sP-selectin detects about 60% at 5% FPR. When PlGF is used in combination with sP-Selectin performance increases remarkably also with LO-PE (Table 1, lines 53, 54 and 55).

The method as disclosed herein has considerable benefits both considering screened populations and health-care decision-making, and also considering individuals; their habits, concern and even anxiety during pregnancy. In population level, cost savings are achieved by adjusting the frequency of visits to midwife or obstetrician relative to predicted severity of possible hypertensive disorder.

Data Analysis Principles
Data are divided to different gestational week areas: 10-14, 15-26, 27-36 (full weeks)
Concentrations (MoMing) in each gestational areas (MoM1-3) are normalized. Covariates; gestational age, mother's weight, ethnicity and smoking
Logistics regression based risk models for different outcomes within each gestational week area are calculated
Variable=analyte MoM
Combinations up to three analytes
Detection rates with different false positive rates and plot ROC curves to all models are calculated.
The indications and the subgrouping are the following:
Pre-eclampsia (PE)
All
With or without chronic hypertension (superimposed PE)
Early or Late (separated by delivery gestational age to be before and after 34 week)
Early with or without chronic hypertension
Late with or without chronic hypertension

EXAMPLES

Example 1

FIGS. 1a shows PlGF measured from normotensive women who later develop EO-PE.

FIG. 1a Box- and whisker plots show that PlGF concentration is decreased in normotensive women who later in the pregnancy develop EO-PE compared to pregnancies that do not have EO-PE (control group). The closer the sample is taken to the onset of the disease, the more decreased PlGF concentration is.

Control means normal pregnancies with no adverse outcomes.

Control including "not normals" means pregnancies that do not develop EO-PE but who might suffer other adverse outcomes of pregnancies.

GA means gestational age at the time of blood draw.

Figure 1B:
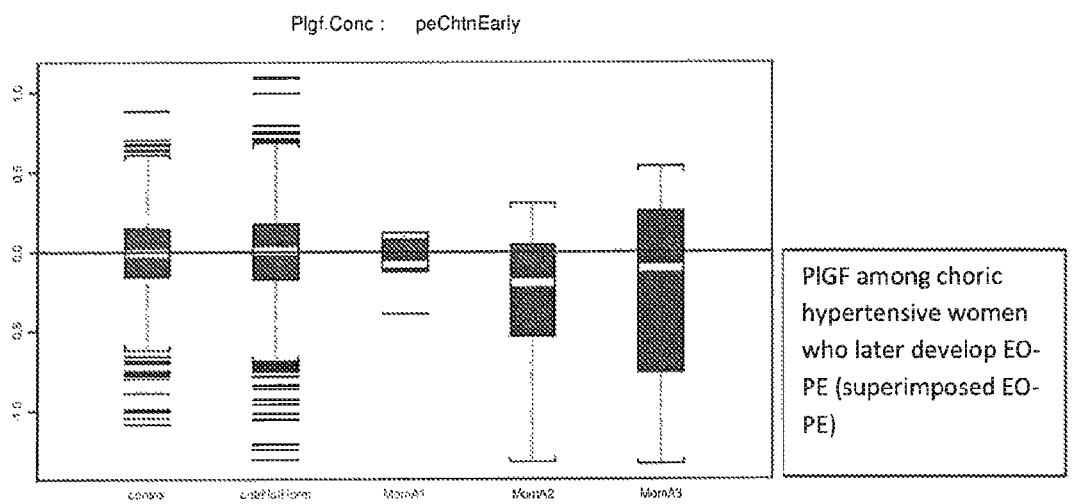
FIG. 1b shows PlGF among chronic hypertensive women who later develop EO-PE (superimposed EO-PE).

FIG. 1b shows PlGF among chronic hypertensive women who later develop EO-PE (superimposed EO-PE).

FIG. 1b Box-and whisker plots show that PlGF concentration does not decrease in women who suffer from chronic hypertension and who later in the pregnancy develop superimposed EO-PE to the same extend than among normotensive women.

Superimposed PE on chronic hypertension: New-onset proteinuria in a women with hypertension before 20 weeks of gestation. It can be characterized by:
A sudden increase in proteinuria if already present in early gestation
A sudden increase in hypertension
The development of HELLP syndrome
Women with chronic hypertension who develop headache, scotomata, or epigastric pain.

FIG. 2 shows PlGF prediction of superimposed EO-PE.

Figures 2A, 2B:
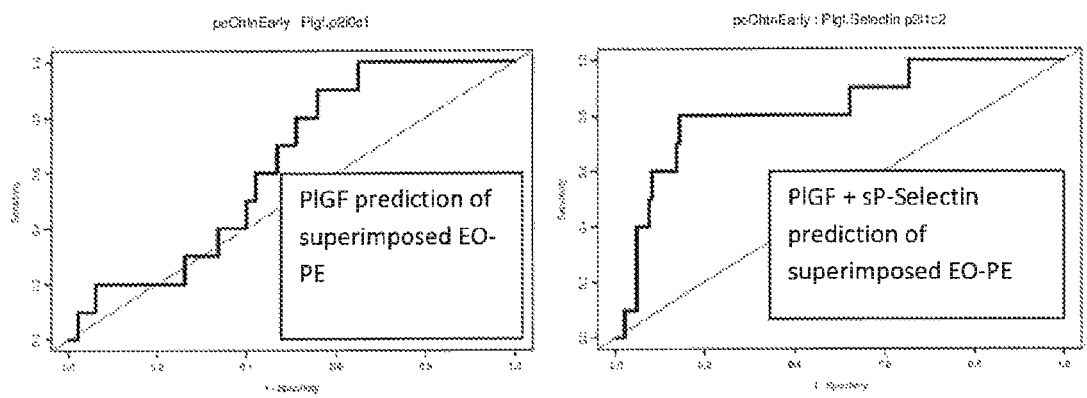
FIGS. 2a shows PlGF prediction of superimposed EO-PE.
FIG. 2b shows PlGF+sP-selectin prediction of superimposed EO-PE.

FIG. 2a is Receiver-Operating Characteristic (ROC) curve of PlGF for prediction of EO-PE among hypertensive women (superimposed PE). FIG. 2a shows PlGF prediction of superimposed EO-PE.

FIG. 2b shows PlGF+sP-selectin prediction of superimposed EO-PE.

FIG. 2b. ROC curve of combination of PlGF+sP-Selectin for prediction of superimposed EO-PE. FIG. 2b shows PlGF+sP-Selectin prediction of superimposed EO-PE.

From the results can be concluded that:
PlGF is a poor marker to predict superimposed EO-PE. When used in combination with sP-Selectin performance increases remarkably. Marker combination detects about 60% of cases at 10% FPR when measured during the $1^{st}$ trimester of pregnancy while PlGF alone detects only about 20% of those women who will develop superimposed EO-PE.

Figure 3:
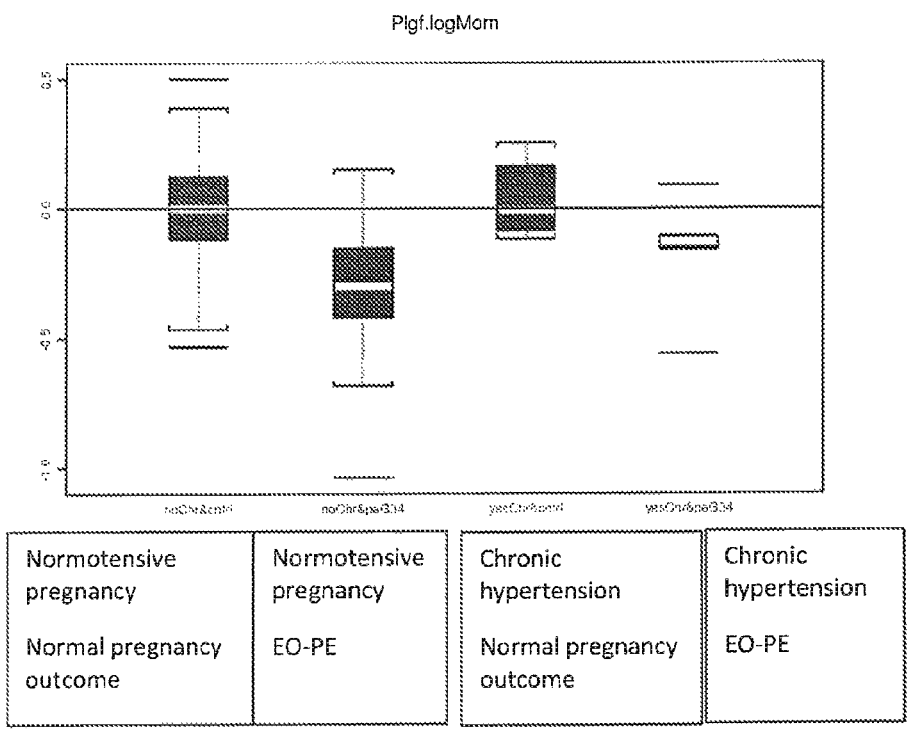
FIG. 3 shows PlGF MoMs among normotensive and chronic hypertensive pregnancies with normal (control group) and EO-PE case. Samples taken at GA 11-13.

Another dataset confirms above results:

FIG. 3 shows PlGF MoMs among normotensive and chronic hypertensive pregnancies with normal (control group) and EO-PE case. Samples taken at GA 11-13.

Figure 4:
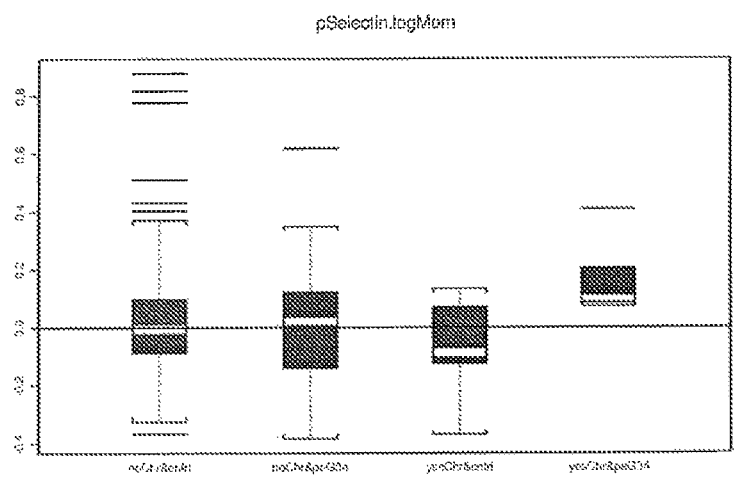
FIG. 4 shows sP-Selectin MoMs among normotensive and chronic hypertensive pregnancies with normal (control group) and EO-PE cases. Samples taken at GA 11-13.

FIG. 4 shows sP-Selectin MoMs among normotensive and chronic hypertensive pregnancies with normal (control group) and EO-PE cases. Samples taken at GA 11-13.

Figure 5:
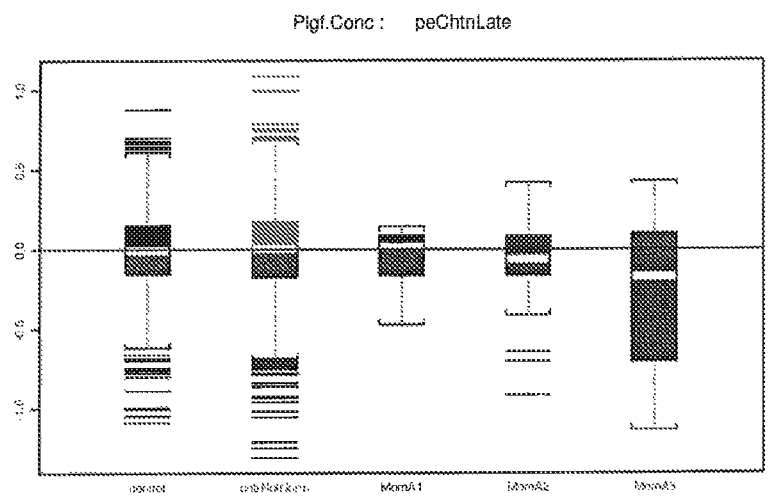
FIG. 5 shows PlGF among women who later develop "typical" PE. Data shows that PlGF as a single marker works better in normotensive women than among chronic hypertensive women just like with EO-PE.

FIG. 5 shows PlGF among women who later develop "typical" PE. Data shows that PlGF as a single marker works better in normotensive women than among chronic hypertensive women just like with EO-PE.

Figure 6:
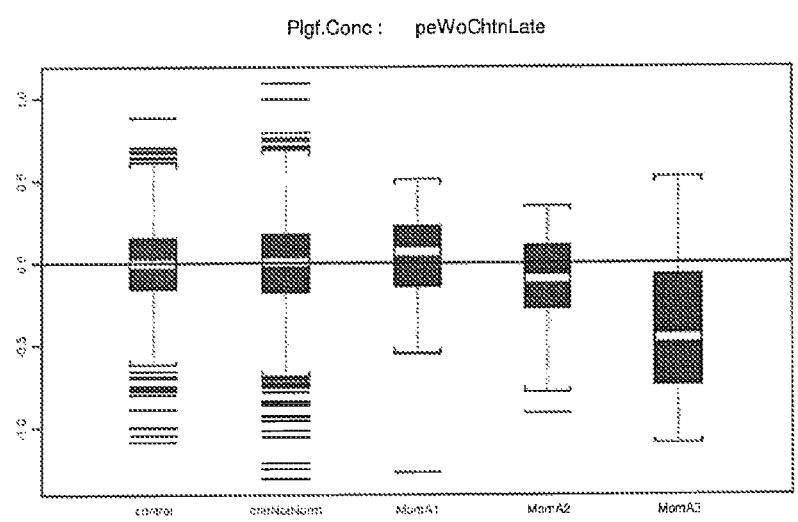
FIG. 6 shows PlGF and superimposed PE.

FIG. 6 shows PlGF and superimposed PE.

FIG. 7 Table 1

The invention claimed is:

1. A method of treating a pregnant individual with chronic hypertension identified as at risk for developing superimposed early onset pre-eclampsia, the method consisting of the steps:
   (a) detecting chronic hypertension in a pregnant individual;
   (b) collecting at least one blood sample from the individual within a first trimester;
   (c) detecting levels of Placental growth factor (PlGF) and sP-selectin in the at least one blood sample; and
   (d) identifying the pregnant individual as having an increased risk of superimposed early onset pre-eclampsia if both of the following occur: the detected level of PlGF in the at least one blood sample is decreased as compared to a level of PlGF in a control sample, and the detected level of sP-Selectin in the at least one blood sample is increased as compared to a level of sP-selectin in a control sample; and
   (e) treating the identified pregnant individual with aspirin to lower the pregnant individual's risk of superimposed early onset pre-eclampsia.

* * * * *